(12) United States Patent
Mitko (10) Patent No.: US 9,772,307 B2
(45) Date of Patent: Sep. 26, 2017

(54) SHUTTER FOR AN ION MOBILITY SPECTROMETER

(71) Applicant: Eye On Air B.V., Enschede (NL)

(72) Inventor: Sergei Vasiljevitsj Mitko, Enschede (NL)

(73) Assignee: Eye On Air B.V., Encshede (NL)

(*) Notice: Subject to any disclaimer, the term of this patent is extended or adjusted under 35 U.S.C. 154(b) by 0 days.

(21) Appl. No.: 15/319,239

(22) PCT Filed: Jun. 11, 2015

(86) PCT No.: PCT/NL2015/050427
§ 371 (c)(1),
(2) Date: Dec. 15, 2016

(87) PCT Pub. No.: WO2015/194943
PCT Pub. Date: Dec. 23, 2015

(65) Prior Publication Data
US 2017/0138903 A1 May 18, 2017

(30) Foreign Application Priority Data

Jun. 16, 2014 (NL) .................................. 2013000

(51) Int. Cl.
*G01N 27/62* (2006.01)
(52) U.S. Cl.
CPC ................... *G01N 27/622* (2013.01)
(58) Field of Classification Search
USPC ....................... 250/286, 281, 282
See application file for complete search history.

(56) References Cited

U.S. PATENT DOCUMENTS

| 6,509,562 B1* | 1/2003 | Yang | G01N 27/622 |
| | | | 250/287 |
| 2007/0187591 A1* | 8/2007 | Bromberg | H01J 49/40 |
| | | | 250/290 |

(Continued)

FOREIGN PATENT DOCUMENTS

WO    2005086742    9/2005

OTHER PUBLICATIONS

Written Opinion of the International Search Authority dated Dec. 23, 2015, received for International Application No. PCT/NL2015/050427.

(Continued)

*Primary Examiner* — Kiet T Nguyen
(74) *Attorney, Agent, or Firm* — Fleit Gibbons Gutman Bongini Bianco PL; Jon A. Gibbons (57) ABSTRACT

The invention relates to a shutter for an ion mobility spectrometer (20), the shutter comprising: a first electrode surface (11) with a number of first electrode elements arranged in the first plane and at a distance from each other; a second electrode surface (12) arranged parallel to and at a distance from the first electrode surface and having a number of second electrode elements arranged in the second plane and at a distance from each other; means for applying a potential difference between the first electrode elements and the second electrode elements, and a third electrode surface (13) with a number of third electrode elements arranged in the third plane and at a distance from each other, wherein the third electrode surface is arranged parallel to and at a distance from the first electrode surface and wherein the third electrode surface is arranged on the opposite side of the first electrode surface relative to the second electrode surface.

9 Claims, 5 Drawing Sheets

(56) References Cited

U.S. PATENT DOCUMENTS

2008/0179515 A1    7/2008  Sperline
2015/0108345 A1*   4/2015  Fujita .................... H01J 49/062
                                                        250/286

OTHER PUBLICATIONS

Denson, S., "Improving the sensitivity and resolution of minature ion mobility spectrometers with a capacitvie trans-impedance amplifier", A dissertation submitted to the Faculty of the Department of Chemistry in partial fulfillment of the requirements for the Degree of Doctor of Philosophy in the Graduate College of the University of Arizona, Jan. 1, 2005, pp. 1-280.

* cited by examiner

SHUTTER FOR AN ION MOBILITY SPECTROMETER

FIELD

The invention relates to a shutter for an ion mobility spectrometer, comprising a first electrode surface with a number of first electrode elements arranged in the first plane and at a distance from each other; a second electrode surface arranged parallel to and at a distance from the first electrode surface and having a number of second electrode elements arranged in the second plane and at a distance from each other; and a circuit for applying a potential difference between the first electrode elements and the second electrode elements. Such a shutter is known as a Tyndall-Powell shutter.

BACKGROUND

In ion mobility spectrometry molecules for analysis are ionised and subsequently carried to a shutter due to a general potential difference in the spectrometer. By applying a reverse potential difference between the first electrode elements and the second electrode elements, that is to say a potential difference that is opposite to the general potential difference, the shutter is closed and prevents the ions from passing through towards the collector plate of the spectrometer. If, on the other hand, a forward potential difference is applied over the first and second electrode elements, that is to say in the same sense as the general potential difference in the spectrometer, the shutter is opened and allows the ions to pass through and continue further on their way in the direction of a collector plate.

When the potential difference over the first and second electrode elements is briefly switched from reverse to forward then back to reverse, that is to say the shutter is briefly opened then closed, short bursts of ions are emitted in the direction of the collector plate through the so-called drift space.

An electric field or drift potential is applied over this drift space between the shutter and the collector plate, whereby the ions will migrate in the direction of the collector plate. Since different types of ion have a different displacement velocity within the drift potential, this being referred to as ion mobility, a swarm of one type of ions will arrive at the collector plate at a different time from a swarm of another type.

On the basis of the time taken by a swarm of ions to move from the shutter to the collector plate, also referred to as the drift time, it is possible to determine which type of ions, and therefore which molecules, are involved.

The drawback of the known shutter is however that, when the shutter is briefly opened and closed again, a relatively elongate swarm of ions is ejected in the direction of the collector plate. In order to enable measurement of the difference in drift times between the different types of ions it is necessary for the swarms of different ions to be wholly pulled apart over the length of the drift space as a result of the specific ion mobility. Because the swarm of ions ejected through the shutter is elongate, a considerable length is thus required for the drift space. This length usually amounts to at least about 4 to 20 centimeters.

An additional drawback of this length of the drift space is that the housing of this space must comply with highly specific design requirements in order to obtain a uniform potential difference through the space.

Another drawback of the known shutter is that the shape of the ejected swarm of ions has an irregular form. This shape resembles to some extent the shape of a stingray. The detection curve of a swarm of specific ions on the collector plate will hereby be erratically shaped, whereby it is more difficult to distinguish different drift times of the different swarms of ions from each other.

All these above stated drawbacks make it difficult to reduce the size of known ion mobility spectrometers.

PRIOR ART

In a PhD Thesis by Stephen Charles Denson entitled "Improving the sensitivity and resolution of Miniature Ion Mobility Spectrometers with a Capacitive Trans-Impedance Amplifier", (XP055153585), there is disclosed a three component ion-beam shutter. This shutter is stated in the reference to operate in the same manner as a two component compression shutter, except that it uses a third screen of another component capable of providing an even potential gradient across the radius of the drift tube. The voltages on the first (S1) and third (S3) screens are held constant while the voltage on the second (S2) screen (which lies between the first and the second screens) is varied to control the shutter. To close the shutter, the absolute voltage at the screen S2 is set higher than at screens S1 and S2 ($|V_{S1}|<|V_{S2}|>|V_{S3}|$), the reverse potential difference between S1 and S2 preventing ions from reaching the second screen. The shutter is opened by lowering $|V_{S2}|$ so that an even forward potential gradient is applied across the space between screens S1 and S3 ($|V_{S1}|>|V_{S2}|>|V_{S3}|$). The advantage offered by the third screen is claimed to be that the ion concentration does not drop off in the area prior to screen S1 when the shutter is closed. However, as with the Tyndall-Powell shutter, the reference states that the three component shutter must be left open for ions to travel across two shutter stages or the ions will be lost when the shutter closes.

The three-component shutter in this reference still determines the size of the swarm of ions admitted into the drift space by setting the length of time that the shutter is opened and for as long as a forward potential is applied across the three screens, the shutter will remain open and continue to admit ions into the drift space.

SUMMARY

With a view to mitigating the above stated drawbacks of the prior art, the present invention provides a shutter for an ion mobility spectrometer, comprising:

a first electrode surface having a number of first electrode elements arranged in the first plane and at a distance from each other;

a second electrode surface arranged parallel to and at a distance from the first electrode surface and having a number of second electrode elements arranged in the second plane and at a distance from each other;

a third electrode surface having a number of third electrode elements arranged in the third plane and at a distance from each other, the third electrode surface being arranged parallel to and at a distance from the first electrode surface and being arranged on the opposite side of the first electrode surface from to the second electrode surface, and a circuit for setting the voltages at the three electrode surfaces to open and close the shutter;

wherein the circuit serves to close the shutter by setting a voltage at the first electrode surface that is less that the voltages prevailing at the third and second electrodes surfaces and serves to allow some ions to pass through the shutter briefly by setting a voltage at the first electrode surface that is greater than the voltages prevailing at the third and second electrode surfaces.

When the shutter is used in an ion mobility spectrometer, the ions or the ionized molecules will arrive first at the third electrode surface. Once the ions have passed through the third electrode surface, they will arrive at the first and second electrode surfaces which, at least in respect of the closing position of the shutter, operate in the same manner as a Tyndall-Powell shutter.

As soon as the potential between the first and second electrode surfaces is reversed, as in a usual Tyndall-Powell shutter, while the potential of the third electrode surface remains the same, the ions between the first electrode surface and the third electrode surface will be attracted to the third electrode surface, while the ions between the first and second electrode surfaces are propelled in the direction of the drift space.

The result is that only the ions located between the first and second electrode surfaces can thus continue to the drift space, even when the shutter remains open for a considerable time. This is because a supply of further ions is blocked at the third electrode surface.

By arranging a third electrode surface the length of an admitted ion swarm can thus be kept short since no further supply of ions can take place as soon as the shutter is opened.

Now that the length of an ion swarm can be kept short, the swarms of different types of ion will be pulled apart more quickly, whereby the collector plate can be arranged a shorter distance from the shutter, while the same accuracy can be achieved in the detection of the different ion swarms.

It has been found in addition that the shape of the swarm of ions ejected via the shutter according to the invention is more uniform, in particular more linear and parallel to the collector surface, whereby the time duration in which a swarm of a type of ions is detected is also shorter. As a result a distinction can hereby be made more easily between the different swarms.

In an embodiment of the shutter according to the invention the first, second and/or third electrode elements are elongate. These can be for instance parallel wires or linear conductive layers.

In another embodiment of the shutter according to the invention the first, second and/or third electrode elements are connected to each other within the respective plane and form a grid-like electrode.

A uniform electric field can be formed by using a linear or grid-like electrode, whereby a uniform swarm of ions of a short length can be obtained during opening and closing of the shutter according to the invention.

A preferred embodiment of the shutter according to the invention comprises means for keeping the potential of the second electrode elements and the third electrode elements equal.

Keeping the potential of the second electrode elements and the third electrode elements equal ensures that during opening and closing of the shutter the electric field upstream of the third electrode surface and the electric field in the drift space are minimally affected. This despite the fact that the potential of the first electrode surface is varied during opening and closing.

In yet another embodiment of the shutter, the pitch distance between the first electrode elements is equal to the pitch distance between the second electrode elements.

Because the pitch distance is kept the same, the ions encounter less obstruction from the electrodes and the swarm of ions can more easily be uniformly shaped.

The pitch distance is preferably less than 1 mm and preferably 400 µm, while the distance between the electrodes is less than 500 µm, preferably 200 µm.

In a preferred embodiment of the shutter, the pitch distance between the third electrode elements is 3 to 10 times smaller than the pitch distance between the first electrode elements.

In the case the pitch distance between the first electrode elements is 200 µm, the pitch distance between the third electrode elements lies between 66 µm and 20 µm.

A further embodiment of the shutter further comprises:
  a first plate-like carrier provided with a large number of openings;
  an electrically conductive layer which is arranged on a first side of the plate-like carrier and which forms the first electrode elements;
  an electrically conductive layer which is arranged on a second side opposite the first side and which forms the second electrode elements;
  a second plate-like carrier which is provided with a large number of openings and wherein both sides are provided with an electrically conductive layer which form the third electrode elements; and
  a spacer arranged between the first plate-like carrier and the second plate-like carrier.

A high dimensional accuracy can be obtained easily by arranging the electrodes as an electrically conductive layer on a plate-like carrier, such as for instance a glass layer. This contributes toward a uniform electric field and, as a result, the forming of a uniform swarm of ions.

In addition, the shutter can be easily produced with this embodiment. Manufacture of a plate-like carrier with openings and electrically conductive layers arranged on either side is a proven technique. By also using spacers, which are for instance formed from a plate-like material, the plate-like carriers with the electrode surfaces thereon can be easily arranged at the correct distance and parallel to each other.

The invention further provides an ion mobility spectrometer comprising:
  a shutter according to the invention;
  a collector plate arranged parallel to and at a distance from the second electrode surface for detecting the arrival of ion swarms.

In an embodiment of the ion mobility spectrometer, the shutter is formed with plate-like carriers for the electrode surfaces, and further comprises a second spacer arranged between the shutter and the collector plate.

Such an embodiment of an ion mobility spectrometer can be produced in simple and compact manner. It is hereby possible to make compact devices with which diverse substances can be detected very accurately. An example of an application of an ion mobility spectrometer of the invention is the detection of unauthorized substances, in particular explosives, in the luggage of aircraft passengers.

These and other features of the invention are further elucidated with reference to the accompanying drawings, in which.

Figure 1A:
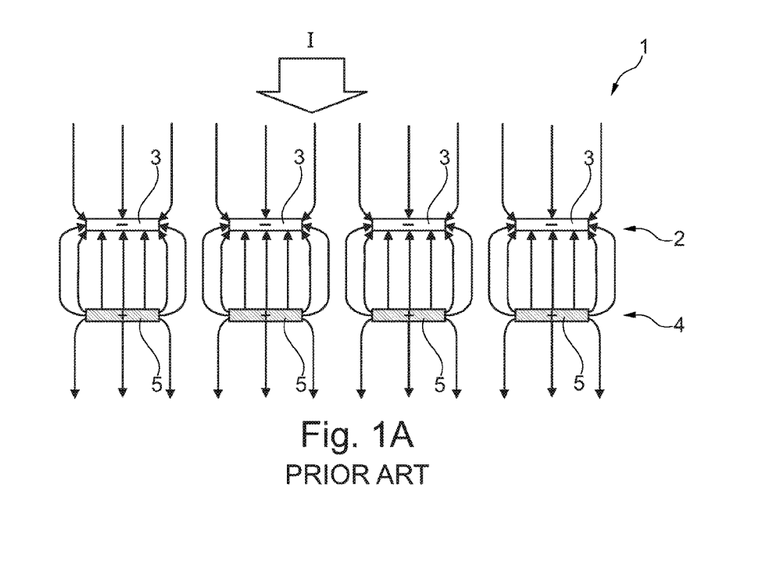
FIGS. 1A and 1B show schematically a prior art shutter.
Figure 1B:
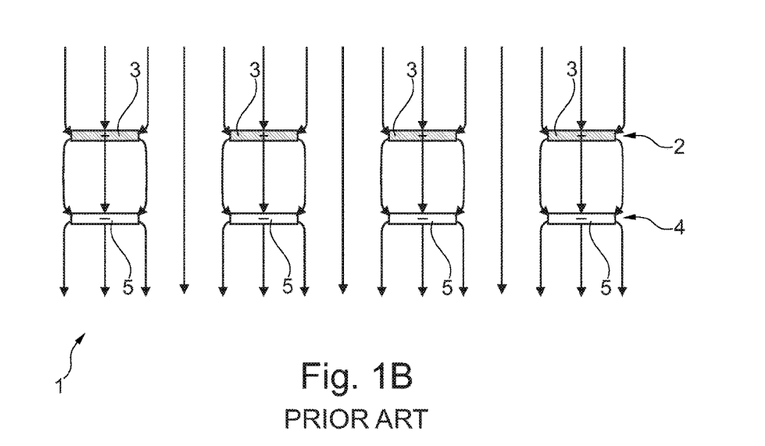

FIGS. 1A and 1B show schematically a prior art shutter which operates in accordance with the above-mentioned Tyndall-Powell principle. This prior art shutter 1 has a first electrode surface 2 with a number of elongate first electrode elements 3 arranged at a distance from each other. The second electrode surface 4 is arranged at a distance from first electrode surface 2. This second electrode surface 4 likewise has a number of elongate second electrode elements 5 arranged at a distance from each other.

In FIG. 1A, the shutter 1 is in the closed position in that between first electrode elements 3 and second electrode elements 5 a reverse potential difference is applied in the opposite direction to the direction I from which the ions are supplied.

In FIG. 1B the potential difference between first electrode elements 3 and second electrode elements 5 is the same direction as the forward direction I, whereby the ions can pass through shutter 1.

Immediately following opening and re-closing of shutter 1 a swarm of ions will be formed which, as already stated above, is erratic.

Figure 2A:
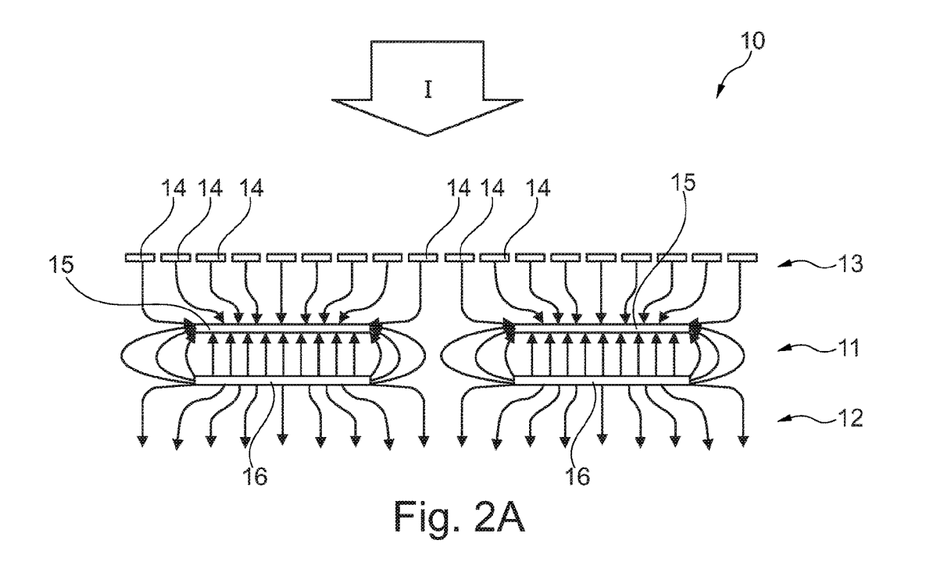
FIGS. 2A and 2B show schematically an embodiment of a shutter according to the invention.
Figure 2B:
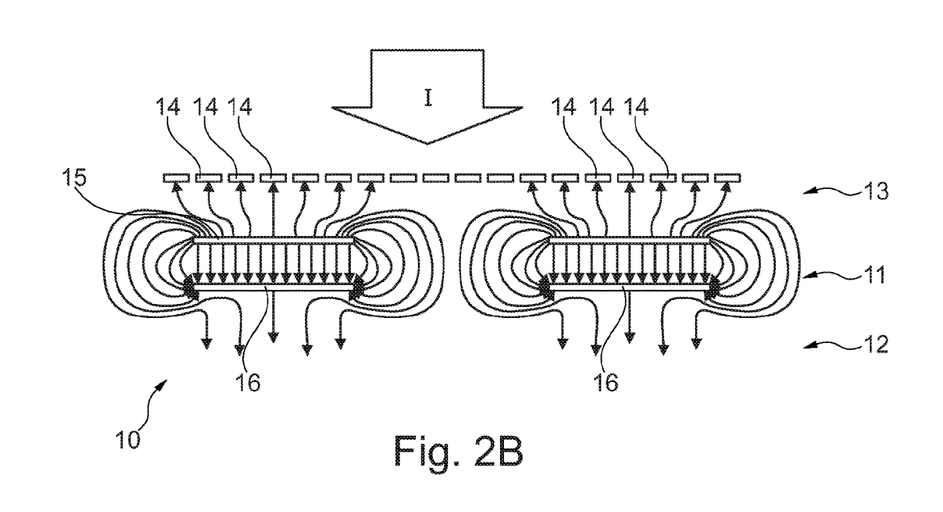

FIGS. 2A and 2B show schematically an embodiment of shutter 10 according to the invention. Shutter 10 has a first electrode surface 11, a second electrode surface 12 and a third electrode surface 13, each arranged parallel to each other.

Electrode elements 14 of third electrode surface 13 preferably have a smaller pitch distance than first electrodes 15 and second electrodes 16.

In FIG. 2A shutter 10 is in the closed position in that a reverse potential difference is applied between first electrode surface 11 and second electrode surface 12, i.e. in opposite direction to the supply direction I of the ions.

In FIG. 2B the shutter is moved into opened position, wherein the potential difference between first electrode surface 11 and second electrode surface 12 is switched to a forward direction. The potential of third electrode surface 13 has however been maintained constant here, so that a reverse potential difference is applied between first electrode surface 11 and third electrode surface 13 preventing the flow of ions past the third electrode surface 13.

So even though shutter 10 is in the opened position, ions cannot pass freely through shutter 10 from supply direction I. Only some of the ions which were present between first electrode surface 11 and second electrode surface 12 can continue on their way.

Figure 3:
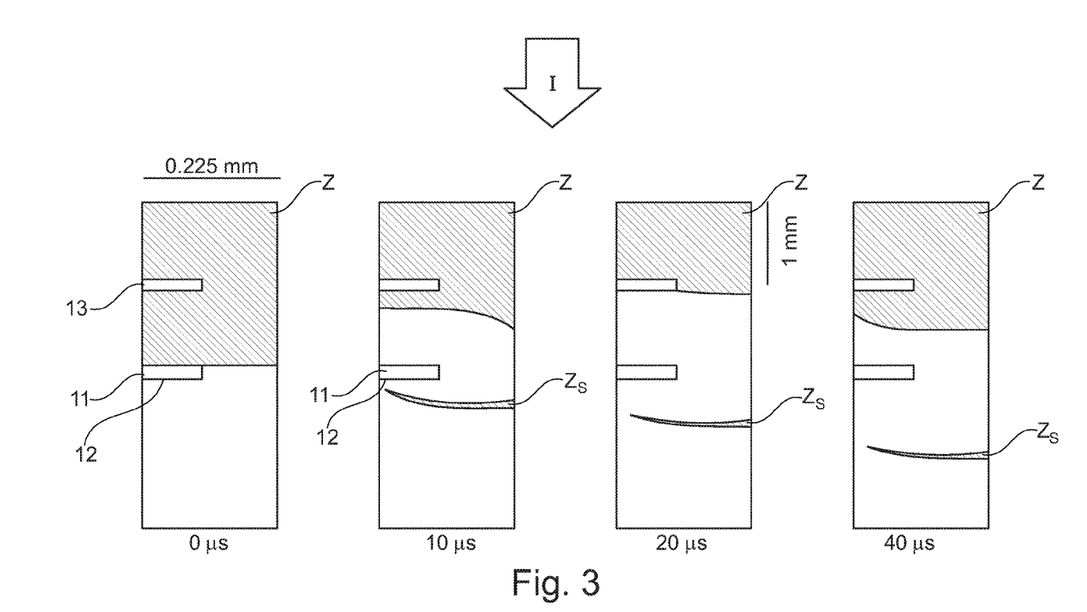
FIG. 3 shows a schematic representation of a swarm of ions over a period of time following opening of the shutter according to FIG. 2.

FIG. 3 shows a schematic representation of a swarm of ions over a period of time following opening of shutter 10.

At 0 μs the potential difference between first electrode surface 11 and second surface 12 is switched to a forward direction. Because the potential difference between first electrode surface 11 and third electrode surface 13 is now in the reverse direction, the ion swarm Z will largely move back onto the third electrode surface 13 (see 10 μs and 20 μs).

Only a small part $Z_s$ of the ion swarm Z will be repelled by second electrode surface 12 in direction I so that these ions can continue on their way.

The shape of the thus formed continuing ion swarm $Z_s$ is uniform and more or less linear. The length in direction I is moreover considerably more limited than in the prior art.

Shutter 10 can in principle remain open as long as desired. In FIG. 3 the potential difference between first electrode surface 11 and second electrode surface 12 is once again switched at 40 μs to close the shutter 10, so that the shutter returns once again to the situation as shown at 0 μs.

Figure 4:
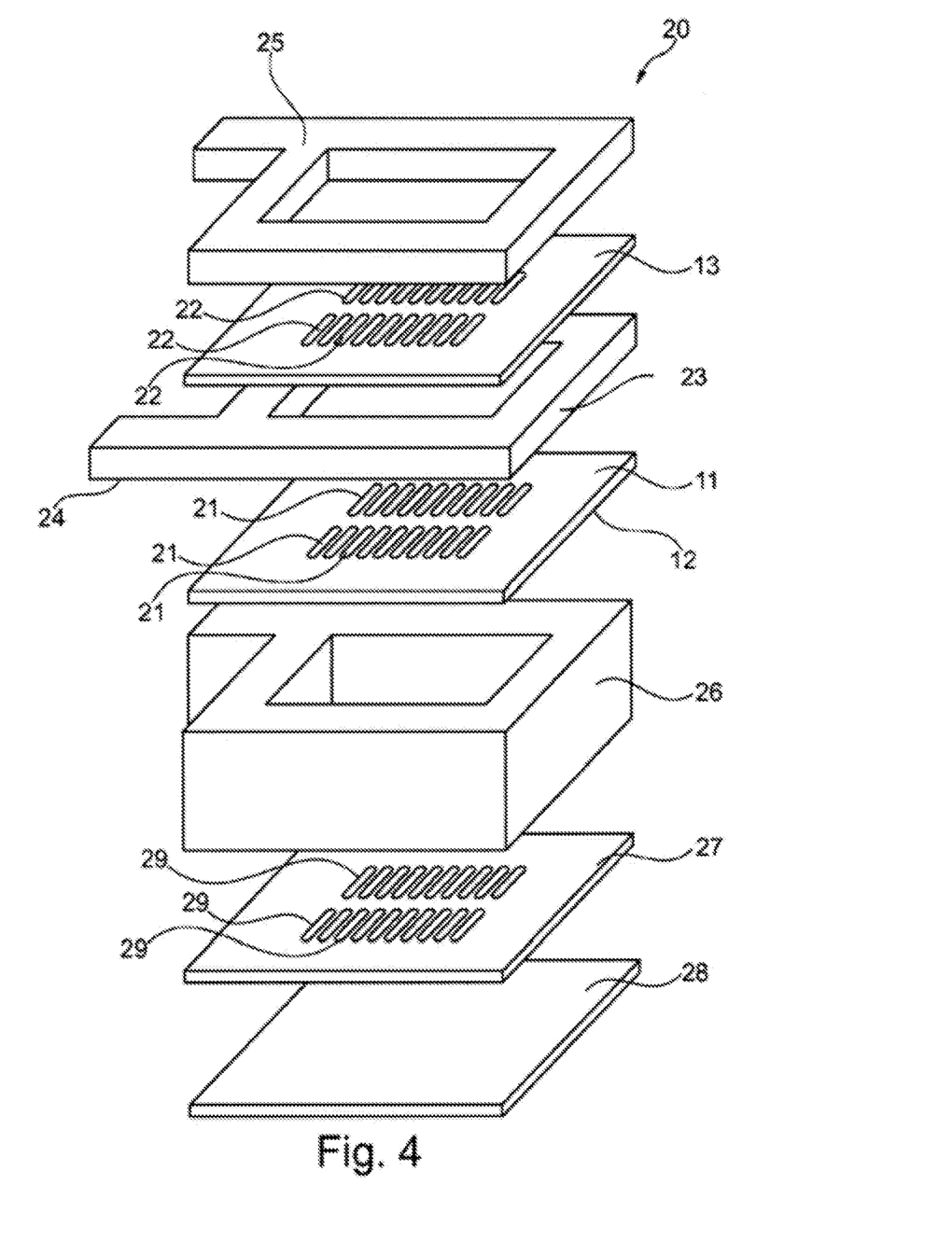
FIG. 4 shows a perspective view with exploded parts of an embodiment of an ion mobility spectrometer.

FIG. 4 shows a perspective view with exploded parts of an embodiment 20 of an ion mobility spectrometer according to the invention.

The ion mobility spectrometer comprises a shutter having a first electrode surface 11, a second electrode surface 12 and a third electrode surface 13.

The first and second electrode surfaces 11, 12 are formed as electrically conductive layers on a plate-like carrier which is provided with openings 21. Third electrode surface 13 is also provided on a plate-like carrier with openings 22.

Provided between the first plate-like carrier with openings 21 and the second plate-like carrier with openings 22 is a spacer 23 which can also comprise a connection 24 for providing first electrode surface 11 with a potential.

A metal electrode 25 is further provided to contact the plate-like carrier with openings 22 in order to provide third electrode surface 13 with a potential.

Provided under second electrode surface 12 is a second spacer 26 which forms the drift space. Provided under this spacer 26 is another plate-like carrier 27 with openings 29 which is also referred to as the collector grid, with collector 28 thereunder which can detect the arrival of a swarm of ions.

Figure 5:
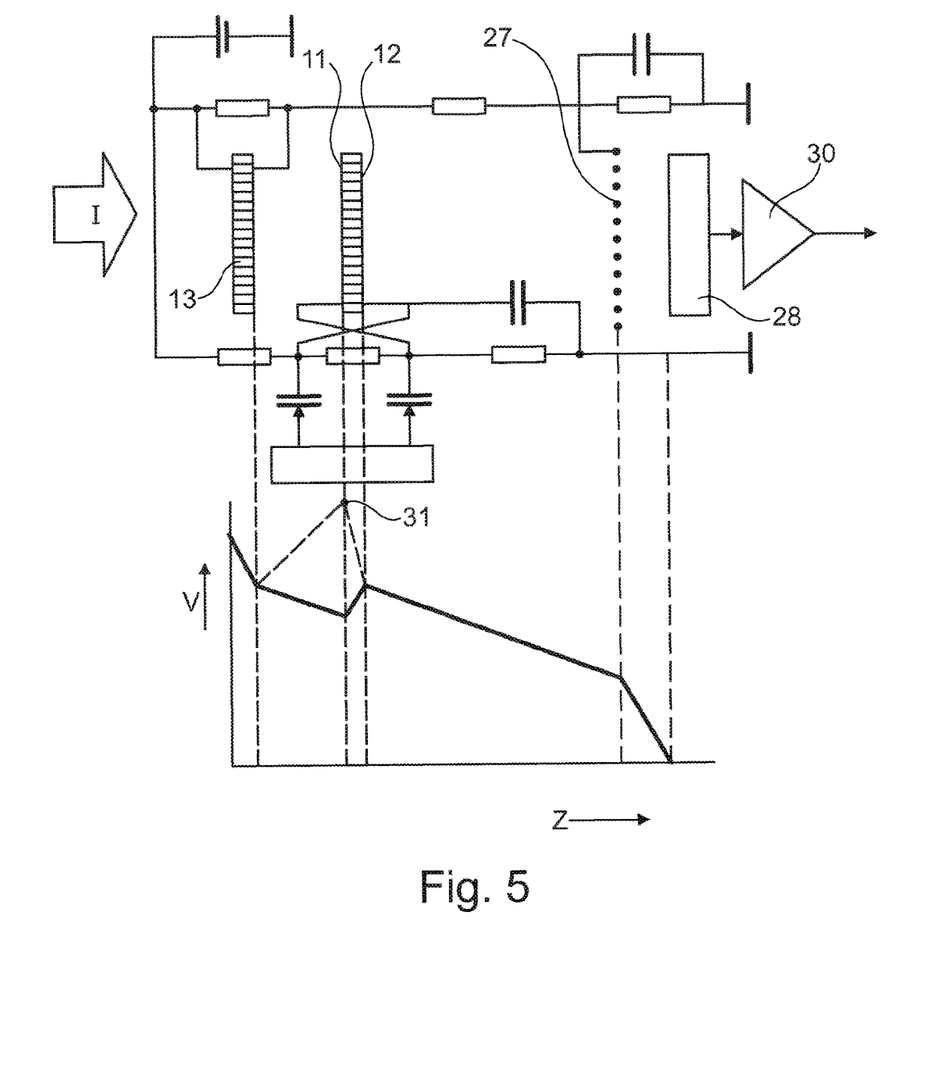
FIG. 5 shows an electrical diagram of the embodiment according to FIG. 4.

FIG. 5 shows an electrical diagram of the embodiment 20 according to FIG. 4. This electrical diagram shows how the different electrode surfaces 11, 12, 13 and collector grid 27 are electrically connected to each other so that a suitable potential drop is obtained over the ion mobility spectrometer 20.

Collector 28 is connected to an amplifier 30 so that the arrival of the swarms of ions can be detected.

In the voltage diagram, the potential variation V is shown along the length Z in the direction of the ion supply I. The full line shows the potential variation V in the closed position of shutter 11, 12, 13, while the broken line shows the potential variation in the opened position of shutter 11, 12, 13.

As can seen from this diagram, the voltage at the third electrode 13 and the second electrode 12 are equal and remain the same both when the shutter is closed (solid line) and when it is open (broken line). Only the voltage on the first electrode 11 is varied to switch between the open and closed states of the shutter. In the closed state, the voltage at the first electrode 11 is below that at the second and third electrodes, whereas in the open state it is greater than the voltage at the other two electrodes.

The peak 31 in the broken line preferably corresponds to a voltage pulse with an amplitude of 300 V, and more preferably of 600 V, the duration of the pulse being 10 μs, or more preferably 20 μs.

The invention claimed is:

1. A shutter for an ion mobility spectrometer, comprising:
a first electrode surface having a number of first electrode elements arranged in a first plane and at a distance from each other,
a second electrode surface arranged parallel to and at a distance from the first electrode surface and having a number of second electrode elements arranged in a second plane and at a distance from each other,
a third electrode surface having a number of third electrode elements arranged in a third plane and at a distance from each other, the third electrode surface being arranged parallel to and at a distance from the first electrode surface and being arranged on opposite side of the first electrode surface from to the second electrode surface, and a circuit for setting voltages at the first electrode surface, the second electrode surface and the third electrode surface to open and close a shutter;

the circuit serving to close the shutter by setting a voltage at the first electrode surface that is less than the voltages prevailing at the third and second electrode surfaces and serving to allow some ions to pass through the shutter briefly by setting a voltage at the first electrode surface that is greater than the voltages prevailing at the third and second electrode surfaces.

2. The shutter as claimed claim 1, wherein the circuit is operative to maintain a potentials at the second and third electrode surfaces equal to one another both when the shutter is open and when it is closed.

3. The shutter as claimed in claim 1, wherein at least one of the first electrode element, the second electrode element and the third third electrode element are elongated.

4. The shutter as claimed in claim 3, wherein the elements of each of the first electrode surface, the second electrode surface and the third electrode surface are connected to each other within a respective plane, each being formed as a grid-like electrode.

5. The shutter as claimed in claim 1, wherein a pitch distance between the first electrode elements is equal to a pitch distance between the second electrode elements.

6. The shutter as claimed in claim 1, wherein a pitch distance between the third electrode elements is 3 to 10 times smaller than a pitch distance between the first electrode elements.

7. The shutter as claimed in claim 1, further comprising
a first plate-like carrier provided with a large number of openings;
an electrically conductive layer which is arranged on a first side of the plate-like carrier and which forms the first electrode elements;
an electrically conductive layer which is arranged on a second side opposite the first side of the plate-like carrier and which forms the second electrode elements;
a second plate-like carrier which is provided with a large number of openings both sides of which are provided with an electrically conductive layer to form the third electrode elements; and
a spacer arranged between the first plate-like carrier and the second plate-like carrier.

8. An ion mobility spectrometer, comprising
a shutter for admitting ions into a drift space and a collector plate arranged parallel to and at a distance from the shutter for detecting an arrival of ions after crossing the drift space, wherein the shutter comprises
a first electrode surface having a number of first electrode elements arranged in a first plane and at a distance from each other;
a second electrode surface arranged parallel to and at a distance from the first electrode surface and having a number of second electrode elements arranged in a second plane and at a distance from each other;
a third electrode surface having a number of third electrode elements arranged in a third plane and at a distance from each other, the third electrode surface being arranged parallel to and at a distance from the first electrode surface and being arranged on a opposite side of the first electrode surface from to the second electrode surface, and
a circuit for setting voltages at the first electrode surface, the second electrode surface and the third electrode surface to open and close the shutter,
wherein the circuit serves to close the shutter by setting a voltage at the first electrode surface that is less than the voltages prevailing at the third and second electrode surfaces and serves to allow some ions to pass through the shutter briefly by setting a voltage at the first electrode surface that is greater than the voltages prevailing at the third and second electrode surfaces.

9. The ion mobility spectrometer as claimed in claim 8, further comprising a second spacer arranged between the shutter and the collector plate.

* * * * *